United States Patent [19]

Yokoyama et al.

[11] Patent Number: 4,733,002

[45] Date of Patent: Mar. 22, 1988

[54] LIPOXYGENASE INHIBITOR

[75] Inventors: Kazumasa Yokoyama; Chikara Fukaya, both of Osaka; Masanori Sugiura, Kyoto; Youichiro Naito, Kyoto; Youichiro Nishida, Kyoto; Tadakazu Suyama, Kyoto, all of Japan

[73] Assignee: Green Cross Corporation, Osaka, Japan

[21] Appl. No.: 737,005

[22] Filed: May 23, 1985

[30] Foreign Application Priority Data

| May 23, 1984 | [JP] | Japan | 59-104998 |
| May 23, 1984 | [JP] | Japan | 59-104999 |
| Jun. 22, 1984 | [JP] | Japan | 59-129530 |
| Jun. 27, 1984 | [JP] | Japan | 59-133496 |
| Aug. 8, 1984 | [JP] | Japan | 59-166981 |
| Aug. 31, 1984 | [JP] | Japan | 59-183253 |

[51] Int. Cl.⁴ ............................................. C07L 69/76
[52] U.S. Cl. .................................. 560/55; 560/75; 560/67; 564/170; 568/325; 568/632; 568/644; 568/646; 568/763
[58] Field of Search ................. 560/55, 67, 75; 564/170; 568/325, 632, 644, 646, 763; 514/532, 622

[56] References Cited

FOREIGN PATENT DOCUMENTS

31561A2  7/1981  European Pat. Off. .
0081321  6/1983  European Pat. Off. .
0092136 10/1983  European Pat. Off. .

OTHER PUBLICATIONS

Koshihara, Y. et al., Biochemica et Biophysica Acta, 792(1), 1984, 92–97.

Primary Examiner—Paul J. Killos
Attorney, Agent, or Firm—Sughrue, Mion, Zinn, Macpeak and Seas

[57] ABSTRACT

A lipoxygenase inhibitor comprising as active ingredient a substituted styrene derivative having a radical of the general formula

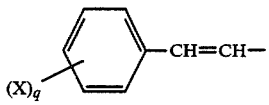

wherein X denotes a hydroxyl group or a lower alkoxy group and q is an integer of 2 or 3, and containing carbon atoms in total of at least 8.

6 Claims, 5 Drawing Figures

LIPOXYGENASE INHIBITOR

BACKGROUND OF THE INVENTION

1. Field of the Invention

The present invention relates to lipoxygenase inhibitors, particularly, to 5-lipoxygenase inhibitors.

2. Description of the Prior Art

5-Lipoxygenase is an enzyme participating in biosynthesis of leukotrienes and 5-hydroxyeicosatetraenoic acid (5-HETE) which are considered taking part in occurrence of allergic symptoms, asthma, inflammation and the like.

Accordingly, compounds having 5-lipoxygenase inhibiting activity are useful for remedy and prevention of allergic symptoms, asthma, inflammation and the like, and development of effective 5-lipoxygenase inhibitors is desired earnestly.

The present invention aims at providing 5-lipoxygenase inhibitors.

Although caffeic acid and its methyl ester are known as substances having 5-lipoxygenase inhibiting activity [Biochim. Biophys. Acta 792, 92 (1984)], their inhibiting activity is not a satisfactory one.

Under such circumstances, the inventors of the present invention have made various investigations with a view to obtain compounds having superior 5-lipoxygenase inhibiting activity, and found that substituted styrene derivatives having a radical of the general formula (I)

wherein X denotes a hydroxyl group or a lower alkoxy group and q is an integer of 2 or 3, and containing carbon atoms in total of at least 8, preferably, of 12 [hereinafter, called as substituted styrene derivatives (II)], have a strong 5-lipoxygenase inhibiting activity.

SUMMARY OF THE INVENTION

Thus, the present invention provides lipoxygenase inhibitors comprising as an active ingredient a substituted styrene derivative having a radical of the general formula wherein X denotes a hydroxyl group or a lower alkoxy group and q is an integer of 2 or 3, and containing carbon atoms in total of at least 8.

BRIEF DESCRIPTION OF THE DRAWINGS

Each of FIGS. 1 to 5 is a graph showing an enzyme activity inhibiting effect against 5-lipoxygenase of the substituted styrene derivatives (II) as shown hereinunder.

In each Figure, the inhibition curve of caffeic acid (I) used as control is also shown.

17.

DESCRIPTION OF THE PREFERRED EMBODIMENT

In the present specification, "a lower alkoxy group" means usually an alkoxy group having 1 to 4 carbon atoms, such as methoxy, ethoxy, n-propoxy, iso-propoxy, n-butoxy, t-butoxy or the like.

In the general formula (I), "$(X)_q$-" means that 2 or 3 substituents represented by X- are bonded to the phenyl group. However, it is preferable that these 2 to 3 substituents are bonded to the phenyl group in the radical (I) at positions adjacent to one another. Further, q is preferably an integer of 2 and the positions of the substituents X's are preferably m- and p- of the phenyl group. Each substituent X may be different from one another.

The substituted styrene derivatives (II) used according to the present invention usually have a hydrocarbon residue, a carboxyl group, an ester group, an amide group, an ether group, a carbonyl group and the like, in addition to the radical of the above-mentioned general formula (I).

The number of total carbon atoms of said substituted styrene derivatives (II) is at least 8, preferably at least 12, and it is preferably 30 or less although there is no special upper limit for it.

As examples of the substituted styrene derivatives (II), the following compounds are mentioned:

(i) Compounds (III) represented by the general formula

(III)

wherein $R_1$ denotes an alkyl group having 3 to 10 carbon atoms, which may be substituted by halogen(s), and X and q have the same meaning as mentioned above.

As regards $R_1$, the alkyl group having 3 to 10 carbon atoms may be either a straight chain one or a branched one, and as examples n-propyl, iso-propyl, n-butyl, iso-butyl, t-butyl, n-pentyl, n-heptyl, n-octyl and the like are mentioned.

As the substituent halogen which may be present in the alkyl group $R_1$, chlorine, bromine and the like are mentioned and chlorine is especially preferred. Examples of the —$COOR_1$ moiety containing the alkyl group substituted by halogen include —CO—O—$(CH_2)_3$—$CH_2$—Cl,
—CO—O—$(CH_2)_3$—$CHCl_2$, and the like.

Such compounds (III) can be prepared, for example, by esterifying caffeic acid or its reactive derivative.

As examples of the reactive derivative of caffeic acid, acid halides (acid chloride, acid bromide, etc.), mixed acid anhydrides (ethylchlorocarbonate, etc.), salts (triethylamine, etc.) and the like are mentioned.

The reaction is performed according to the usual esterification reaction. That is, the reaction is carried out usually by heating caffeic acid and a prescribed alcohol under stirring, preferably, in the presence of an acid catalyst.

As the reaction solvent the prescribed alcohol (30 to 100 eq.) is used, and as the acid catalyst p-toluenesulfonic acid, anhydrous hydrochloric acid or the like, preferably anhydrous hydrochloric acid (0.01 to 0.5 eq.).

The reaction temperature is about 80° to 100° C. and the reaction time is about 3 to 4 hours.

(ii) Compounds (IV) of the general formula wherein $R_2$ and $R_3$ each denotes a hydrogen atom, a lower alkoxy group or a hydroxyl group and Z denotes a radical of the formula —O—$(CH_2)_n$—CH=CH—,

—NH—$(CH_2)_n$—CH=CH—, or

—NH—$(CH_2)_n$— wherein n is an integer of 1 to 4.

When the substituents $R_2$ and $R_3$ in the general formula (IV) are hydroxyl groups or alkoxy groups, their positions are preferably at m- and p-positions of the phenyl group.

Such compounds (IV) can be prepared, for example, by reacting caffeic acid or its reactive derivative with a compound of the general formula (V)

wherein Y denotes OH or $NH_2$ and $R_2$, $R_3$ and n have the same meanings as mentioned above, or with a compound of the general formula (VI)

wherein $R_2$, $R_3$ and n have the same meanings as mentioned above.

As the reactive derivative of caffeic acid, the same derivatives as described above as mentioned as examples.

In this reaction, it is preferable to use dicyclohexyl carbodiimide. When the compound (V) is a compound of alcoholic series, it is desirable to protect any phenolic hydroxyl group in the compound (V) with a protecting group such as tetrahydropyranyl group, etc.

The reaction is performed preferably in a solvent such as tetrahydrofuran, acetonitrile and the like, and the reaction temperature is desirably about room temperature to 50° C. And the reaction time is usually about 7 to 20 hours. The molar ratio of caffeic acid, the compound V or VI and dicyclohexyl carbodiimide is usually about 1:1:1.1. The concentration of substrate is about 0.1 to 0.2M.

(iii) Compounds (VII) of the general formula (VII)

wherein m is an integer of 6 to 14 and X and q have the same meanings as mentioned above.

Such compounds (VII) can be prepared for example by reacting caffeic acid or its reactive derivative with a compound of the general formula (VIII)

wherein m has the same meaning as mentioned above.

As the reactive derivative of caffeic acid, the same derivatives as described above are mentioned as examples.

When free caffeic acid is used in the reaction, it is preferable to use a condensing agent, for example, N,N'-disubstituted carbodiimide such as N,N'-dicyclohexyl carbodiimide, or a dehydrating condensing agent such as N,N'-carbonyldiimidazole. When such condensing agent is used, the reaction is considered to progress through a reactive derivative of the carboxylic acid.

The reaction is usually performed in a solvent which does not disturb the reaction, such as tetrahydrofuran, acetonitrile, dimethylformamide and the like. The solvent especially preferred is tetrahydrofuran. The reaction temperature is suitably about room temperature to 50° C. and the reaction time is about 7 to 15 hours. Equal moles of caffeic acid, the compound VIII and N,N'-dicyclohexyl carbodiimide are preferably used and the concentration of substrate is about 0.2M.

(iv) Compounds (IX) of the general formula (IX)

wherein $R_4$ denotes a phenyl group which may be substituted by a hydroxyl group, a lower alkoxy group or a halogen atom, or a hydrogen atom, l is zero or an integer of 1 to 7 and X and q have the same meanings as mentioned above, said l being an integer of 1 to 7 when said $R_4$ denotes a hydrogen atom.

Although l is zero or an integer of 1 to 7, it is preferred that l is an integer of 1 to 7 when $R_4$ is a hydrogen atom, and that l is zero or an integer of 1 to 3 when $R_4$ is a phenyl group which may be substituted.

Such compounds (IX) can be prepared, for example, by reacting a compound (X) of the general formula (X)

wherein X and q have the same meanings as mentioned above, with a compound (XI) of the general formula (XI)

wherein $R_4$ and l have the same meaning as mentioned above.

The reaction is performed usually in a solvent which does not disturb the reaction. As the solvent, an etheral solvent such as tetrahydrofuran, diethyl ether, dimethoxyethane or the like especially tetrahydrofuran, is preferable.

The reaction is performed preferably in the presence of a non-nucleophilic base such as sodium hydride, lithium diisopropylamide or the like. The reaction temperature is usually about −80° C. to room temperature, and the reaction time is usually about 2 to 4 hours. The molar ratio of the compound (X), (XI) and non-nucleophilic base is usually 1:1:1 and the concentration of substrate is about 0.1 to 0.2M.

When the compound (X) and/or the compound (XI) have/has a phenolic hydroxyl group, it is preferable to protect the hydroxyl group beforehand, for example, in the form of methyl ether, tetrahydropyranyl ether or the like.

Such compounds (XI) are prepared, for example, by reacting a compound of the formula (XII)

with a reactive derivative (such as ester or the like) of a compound of the general formula (XIII)

wherein $R_4$ and l have the same meanings as mentioned above.

The reaction is carried out usually under cooling in the presence of a strongly basic metal compound such as n-butyl lithium or the like.

The reaction is performed usually in a solvent such as tetrahydrofuran, diethyl ether, dimethoxyethane or the like. Among them, tetrahydrofuran is preferable.

The molar ratio of the compound (XI), (XIII) and n-butyl lithium is usually about 1:1:1.05. And the concentration of the substrate is about 0.2 to 1.0M.

(v) Compounds (XIV) of the general formula (XIV)

wherein $R_5$ denotes a hydrogen atom or in which $R_6$ and $R_7$ each denotes a hydrogen atom, a hydroxyl group, a lower alkoxy group or a halogen atom, p is an integer of 1 to 8 when $R_5$ is a hydrogen atom, and zero or an integer of 1 to 5 when $R_5$ is and X and q have the same meanings as mentioned above.

Although p is an integer of 1 to 8 when $R_5$ is a hydrogen atom, it is preferred that p is an integer of 3 to 7 when $R_5$ is a hydrogen atom. When $R_5$ is p is preferably an integer of 1 to 3 though it may be zero or an integer of 1 to 5.

$R_6$ and $R_7$ do not give so much influence on the 5-lipoxygenase activity. However, it is preferred that they are a hydrogen atom or a hydroxyl group.

Such compounds (XIV) can be prepared by reacting a compound (X) with a compound of the general formula $$(C_6H_5)_3P=CHC_pH_{2p}-R_5 \qquad (XV)$$

wherein $R_5$ and p have the same meanings as mentioned above.

The reaction is performed usually in a solvent which does not disturb the reaction, such as dimethyl sulfoxide, diethyl ether, tetrahydrofuran, dimethoxy ethane or the like. The solvent especially preferred is dimethyl sulfoxide. The reaction temperature is about 0° to 50° C., and the reaction time is about 2 to 4 hours.

The molar ratio of the compound (X) and (XV) is usually about 1:1.15 and the concentration of the substrate is about 0.2 to 0.4M.

When the compound (X) and/or the compound (XV) have/has a phenolic hydroxyl group, it is preferable to protect the hydroxyl group beforehand, for example, in the form of methyl ether, tetrahydropyranyl ether or the like.

The substituted styrene derivatives (II) have 5-lipoxygenase inhibiting activity, exhibit 5-lipoxygenase inhibiting effect on mammals (human beings, horse, dog, mouse, guinea pig, rat and the like), and accordingly are useful for remedy and prevention of allergic symptoms, asthma, inflammation and the like.

The substituted styrene derivatives (II) are administered perorally or non-perorally.

The 5-lipoxygenase inhibitors of the present invention are administered as such or in the form of medicinal preparations with carriers acceptable pharmaceutically. The preparations are prepared by a process known per se. As examples of the form of preparations, tablets, capsules, powders, suppositories, injections and the like are mentioned.

The substituted styrene derivatives (II) are administered, for example, in the case of oral administration, using in an amount of 10 to 300 mg per day, in one dose or in several divided doses. However, the amount of administration may vary depending on ages, body-weights and/or degree of the disease and reaction to the remedy.

Pharmacological Experiment

Figure 1:
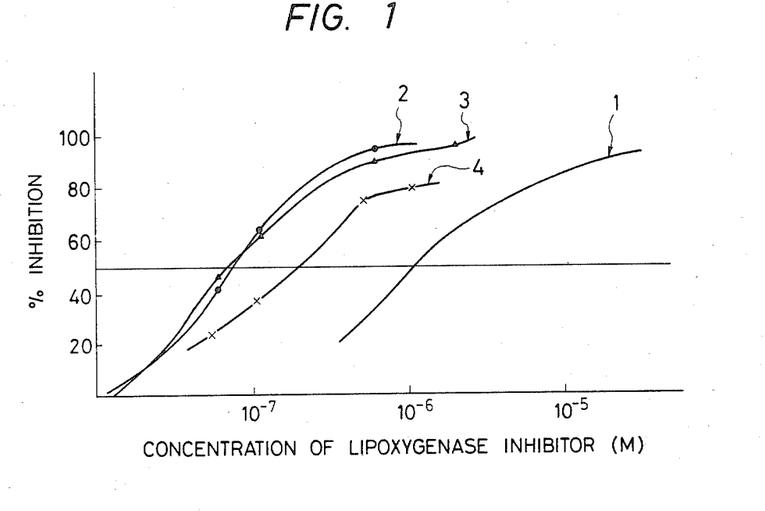
Figure 2:
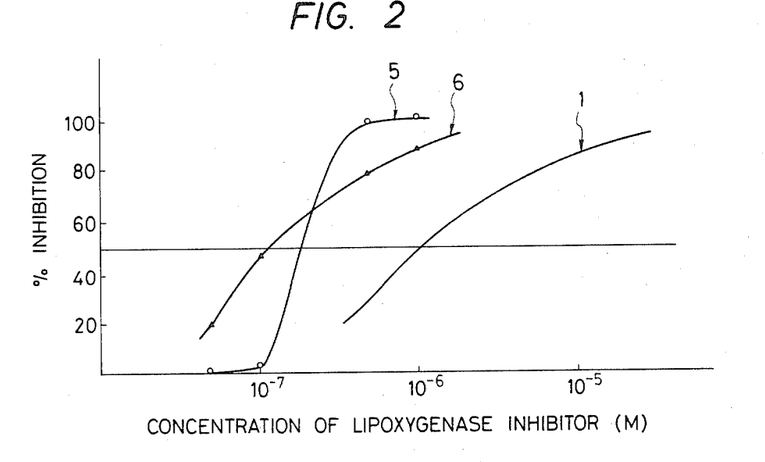
Figure 3:
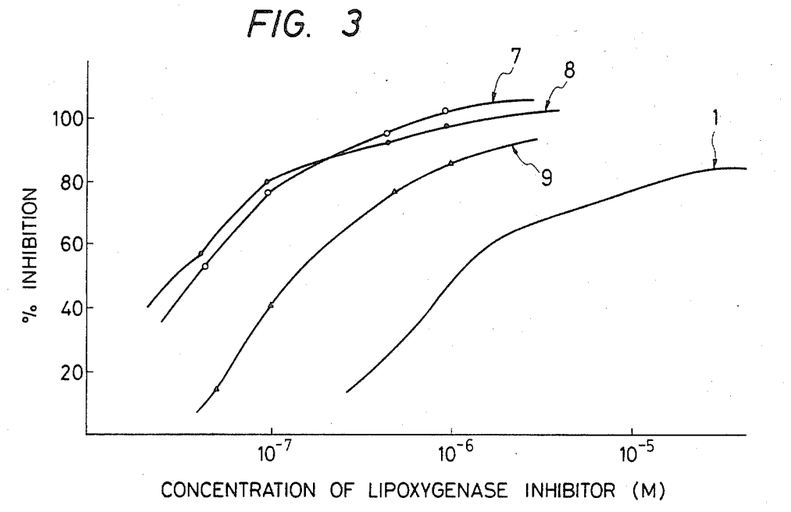
Figure 4:
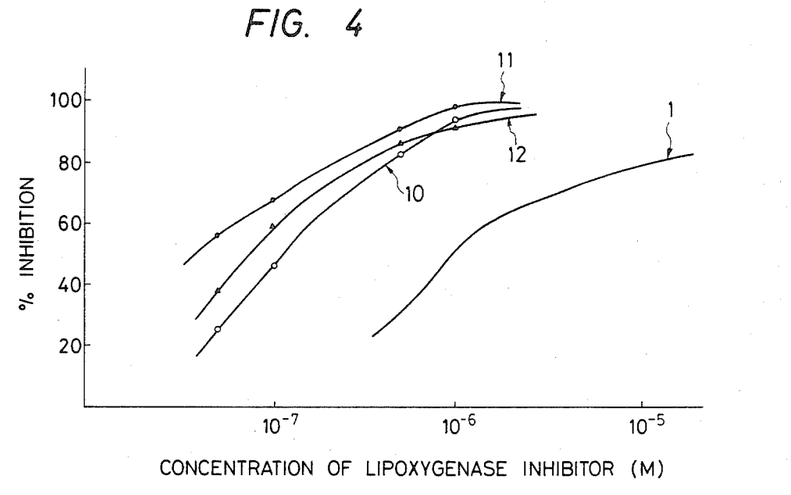
Figure 5:
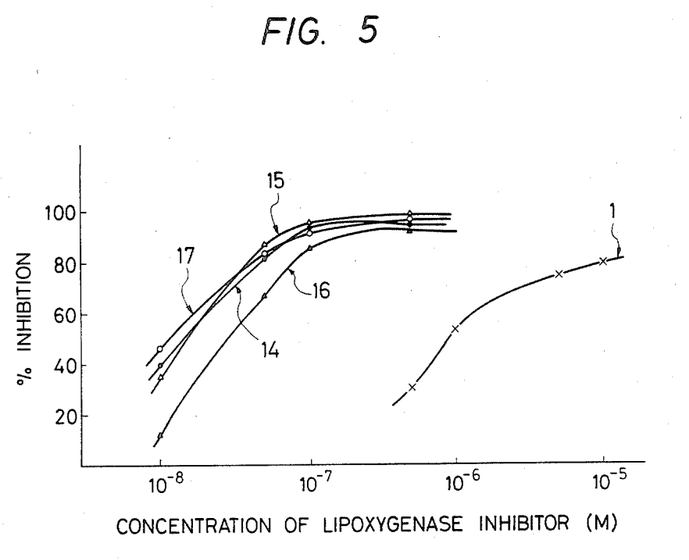

Using polymorphonuclear leukocyte collected from a guinea pig as enzyme source, the enzyme, $^{14}C$-labelled arachidonic acid and a substituted styrene derivative (II) of various kinds and various concentrations were added to a reaction liquid and the reaction was performed for a prescribed time. The 5-HETE and the leukotriene B synthesized from the $^{14}C$-arachidonic acid by 5-lipoxygenase were separated by means of thin layer chromatography, the enzyme activity was pursued by measuring their radioactive counts, and $ID_{50}$ was pursued from the enzyme activity inhibition curve. The results obtained are shown in FIGS. 1 to 5.

Toxicological Experiment

The toxicity against mice of each of the compounds of the present invention is, as administered orally, a $LD_{50}$ value of 100 mg/kg or more. That is, the compounds show a very large $LD_{50}$ value as compared with the amount of administration and have a wide safety range.

Formulation Example

Either one of the substituted styrene derivatives described in the following Examples 1 to 21: 50 mg
Magnesium stearate: 50 mg
Lactose: 50 mg The above ingredients were compounded, and a tablet weighing 150 mg was obtained.

Hereinafter, the present invention is further explained by giving Examples. The invention, however, shall never be limited within the ambit of these Examples.

EXAMPLES 1 TO 3

To 50 ml of butanol into which hydrogen chloride gas was introduced beforehand for about 10 minutes, was added 2 g of caffeic acid. The resulting mixture was heated at 90° to 100° C. and stirred for 3 hours. The reaction product was concentrated under a reduced pressure, and the residue obtained was purified by means of chromatography and then recrystallized from ether/hexane to give 1.4 g of caffeic acid butyl ester.

According to the same manner, caffeic acid propyl ester and caffeic acid pentyl ester were synthesized.

$IR_{\gamma max}^{KBr}$: caffeic acid propyl ester 3500, 3300, 1680, 1602 cm$^{-1}$, caffeic acid butyl ester 3490, 3320, 1682, 1603 cm$^{-1}$, caffeic acid pentyl ester 3500, 3350, 1683, 1605 cm$^{-1}$.

EXAMPLE 4

Preparation of caffeic acid 3,4-dihydroxycinnamyl ester (1) To 6 ml of tetrahydrofuran containing 88 mg of caffeic acid were added 106 mg of dicyclohexyl carbodiimide and 155 mg of 3,4-bistetrahydropyranyloxy-cinnamyl alcohol [synthesized from caffeic acid in 3 steps: (a) esterification (HCl—CH$_3$OH), (b) protection of catechol (dihydropyran, p-toluenesulfonic acid) and (c)

reduction (diisobutyl aluminum hydride)]. The mixture was stirred for 17 hours at room temperature and for 3 hours at 50° C. The reaction mixture was filtered. The filtrate was concentrated and purified by means of column chromatography [silica gel/hexane:ethyl acetate (3:2)] whereby 55 mg of oily caffeic acid 3,4-bis-tetrahydropyranyloxy-cinnamyl ester was obtained.

IR: $\gamma$max 3520, 3200, 1700, 1630, 1600 cm$^{-1}$.

NMR: $\delta$(CDCl$_3$, D$_6$—DMSO), 0.9–2.1 (m, 12H), 3.4–4.3 (m, 4H), 4.75 (d, J=6 Hz, 2H), 5.4 (s, 2H), 6.15 (d, J=15 Hz, 7H), 6.2–7.3 (m, 8H), 7.55 (d, J=15 Hz, 1H).

(2) In 2 ml of absolute methanol was dissolved 55 mg of caffeic acid 3,4-bistetrahydropyranyloxy-cinnamyl ester obtained in the above (1), and a catalytic amount of p-toluenesulfonic acid was added to the solution at 0° C. The mixture was stirred for 1 hour at the same temperature. After the reaction, one drop of triethylamine was added to the resulting mixture and the mixture was concentrated to give crude product. The crude product was purified by means of thin layer chromatography [silica gel/hexane:ethyl acetate (1:3)] to give 15 mg of pure product.

Ir: $\gamma$max 3300, 1680, 1600 cm$^{-1}$

NMR: $\delta$(D$_4$—MeOH), 4.3–4.6 (m, 2H), 5.9 (d, 15 Hz, 1H), 5.85–6.7 (m, 8H), 7.2 (d, 15 Hz, 1H).

EXAMPLE 5

Preparation of caffeic acid benzylamide

To 5 ml of tetrahydrofuran containing 180 mg of caffeic acid were added 206 mg of dicyclohexyl carbodiimide and 107 mg of benzylamine. The mixture was stirred at 50° C. for 6 hours and then filtrated. The filtrate was concentrated and the residue obtained was recrystallized from ethyl acetate/hexane to give 100 mg of granular crystals.

Melting point: 161°–167° C.

IR: $\gamma$max 3250, 1640, 1585 cm$^{-1}$.

NMR: $\delta$(D$_6$—DMSO, CDCl$_3$), 4.45 (d, J=6 Hz, 2H), 6.38 (d, J=14 Hz, 1H), 6.7–7.5 (m, 9H).

EXAMPLES 6 TO 8

Compounds of the following formulae were obtained in accordance with Example 4 or 5:

EXAMPLE 9

Preparation of caffeic acid hexylamide

To 5 ml of tetrahydrofuran containing 180 mg of caffeic acid were added 206 mg of dicyclohexyl carbodiimide and 101 mg of hexylamine. The mixture was stirred at 50° C. for 7 hours and then the reaction mixture was filtrated. The filtrate was concentrated and purified by means of column chromatography (silica gel/hexane:ethyl acetate=1:1). After recrystallization from ethyl acetate/hexane, 100 mg of white crystals was obtained.

Melting point: 141°–143° C.

IR: $\gamma$max 3500, 1645, 1585, 970 cm$^{-1}$.

NMR: $\delta$D$_6$—DMSO, CDCl$_3$), 0.92 (t, J=6 Hz, 3H), 1.0–1.7 (m, 8H), 3.1–3.4 (m, 2H), 6.40 (d, J=15 Hz, 1H), 6.8–7.1 (m, 3H), 7.40 (d, J=15 Hz, 1H).

EXAMPLES 10 AND 11

Caffeic acid octylamide and caffeic acid decylamide were prepared in accordance with Example 9.

Caffeic acid octylamide

Melting point: 119°–121° C.

IR: $\gamma$max 3490, 1645, 1585, 970 cm$^{-1}$.

NMR: $\delta$(D$_4$—MeOH, CDCl$_3$), 0.90 (m, 3H), 1.0–1.7 (m, 12H), 3.3 (m, 2H), 6.30 (d, J=14 Hz, 1H), 6.7–7.1 (m, 3H), 7.41 (d, J=14 Hz, 1H).

Caffeic acid decylamide

Melting Point: 117°–119° C.

IR: $\gamma$max 3500, 1643, 1590, 970 cm$^{-1}$.

NMR: $\delta$(D$_4$—MeOH, CDCl$_3$), 0.90 (m, 3H), 1.0–1.7 (m, 12H), 3.3 (m, 2H), 6.30 (d, J=14 Hz, 1H), 6.7–7.1 (m, 3H), 7.43 (d, J=14 Hz, 1H).

EXAMPLE 12

Using 3,4-dimethoxycinnamic acid, 3,4-dimethoxycinnamic acid octylamide was prepared in accordance with Example 9.

IR: $\gamma$max 1660, 1600, 970 cm$^{-1}$.

NMR: $\delta$(CDCl$_3$), 0.90 (t, J=6 Hz, 3H), 1.0–1.7 (m, 12H), 3.0–3.4 (m, 2H), 3.85 (s, 6H), 6.50 (d, J=15 Hz, 1H), 6.7–7.2 (m, 3H), 7.45 (d, J=15 Hz, 1H).

EXAMPLE 13-(1)

Preparation of 1-(3,4-dimethoxyphenyl)-3-oxo-1-octene

Under cooling with ice, to 70 ml of dry 1,2-dimethoxyethane containing 0.87 g of sodium hydride (50% mineral oil) was added dropwise 30 ml of dry 1,2-dimethoxyethane containing 4.0 g of dimethyl 2-oxoheptylphosphonate. Then, the mixture was stirred at room temperature for 1 hour and, after that, cooled at −30° C. Then, 3 ml of dry 1,2-dimethoxyethane containing 3.0 g of veratraldehyde was added dropwise. After dropping, the temperature was restored slowly to room temperature. Then, the reaction mixture was poured into water and extracted with ethyl acetate. The ethyl acetate layer was washed with water and dried with magnesium sulfate. The solvent was removed by distillation to obtain crude product. After purification of the crude product by means of column chromatography (silica gel/hexane:ethyl acetate=3:1), 1.3 g of the above caption compound was obtained.

IR: $\gamma$max 1685, 1655, 980 cm$^{-1}$.

NMR: $\delta$(CDCl$_3$), 0.90 (t, J=6 Hz, 3H), 1.05–2.0 (m, 6H), 2.61 (t, J=7 Hz, 2H), 3.90 (s, 6H), 6.59 (d, J=16 Hz, 1H), 6.8–7.2 (m, 3H), 7.50 (d, J=16 Hz, 1H).

EXAMPLE 13-(2)

Preparation of 1-(3,4-dihydroxyphenyl)-3-oxo-1-octene

In 1 ml of dry dichloromethane was dissolved 128 mg of 1-(3,4-dimethoxyphenyl)-3-oxo-1-octene obtained in the above Example 13-(1), and the solution was cooled at −78° C. Then, 1.5 ml of 1N boron tribromide solution in dichloromethane was added dropwise to the solution, and the temperature was restored to room temperature slowly. Then, the reaction mixture was poured in ice-water and extracted with ethyl acetate. The ethyl acetate layer was washed with water and dried with magnesium sulfate. The solvent was removed by distillation to give crude product. After recrystallization from water/ethanol, 60 mg of the above caption compound was obtained as crystals.

Melting Point: 130° to 131° C.

IR: γmax 3500, 1678, 1640, 1598, 980 cm$^{-1}$.

NMR: γ(CDCl$_3$), 0.90 (m, 3H), 1.1–1.8 (m, 6H), 2.60 (t, J=6 Hz, 2H), 6.50 (d, J=16 Hz, 1H), 6.7–7.1 (m, 3H), 7.43 (d, J=16 Hz, 1H), 8.99 (s, 1H), 9.37 (s, 1H).

EXAMPLE 14

Preparation of 1,5-bis(3,4-dihydroxyphenyl)-3-oxo-1-pentene

In accordance with the above Examples 13-(1) and 13-(2), 1,5-bis(3,4-dihydroxyphenyl)-3-oxo-1-pentene was obtained, using dimethyl-2-oxo-4-(3,4-dimethoxyphenyl)butylphosphonate instead of the Wittig reagent dimethyl 2-oxoheptylphosphonate used in Example 13-(1).

REFERENTIAL EXAMPLE 1

Preparation of dimethyl 2-oxo-4-(3,4-dimethoxyphenyl)butylphosphonate

To a mixture cooled at −78° C. of 50 ml of 2.1M n-butyl lithium solution in hexane and 100 ml of tetrahydrofuran, was added dropwise 12.4 g of dimethyl methylphosphonate. The mixture was stirred at −78° C. for 30 minutes, and thereafter 22.4 g of methyl 3-(3,4-dimethoxyphenyl)propionate [synthesized from 3,4-dimethoxycinnamic acid in 2 steps: (a) esterification (HCl—CH$_3$OH) and (b) reduction (Pd/C—H$_2$)] and 100 ml of tetrahydrofuran were added dropwise to the mixture. Then, the reaction was continued at −78° C. for 22 hours. The reaction mixture was poured in 500 ml of saturated aqueous sodium chloride solution. After neutralization and extraction with dichloromethane, the extract was dried and concentrated to give crude product. By purification of the crude product by means of column chromatography (silica gel/hexane:ethyl acetate=1:4), 9.0 g of the above caption compound was obtained.

EXAMPLE 15-(1)

Preparation of 1-(3,4-bistetrahydropyranyloxyphenyl)-6-(3,4-dimethoxyphenyl)-3-oxo-1-hexene In accordance with the above Example 13-(1), 1-(3,4-bistetrahydropyranyloxyphenyl)-6-(3,4-dimethoxyphenyl)-3-oxo-1-hexene was obtained.

However, dimethyl 2-oxo-5-(3,4-dimethoxyphenyl)-pentylphosphonate obtained in the same manner as Referential Example 1 was used instead of the Wittig reagent dimethyl 2-oxoheptylphosphonate used in Example 13-(1), and 3,4-bis-tetrahydropyranyloxy-benzaldehyde (synthesized from 3,4-dihydroxy-benzaldehyde and dihydropyran) was used instead of vetratralhyde.

IR: γmax 1685, 1630, 975 cm$^{-1}$.

NMR: δ(CDCl$_3$), 1.2–2.2 (m, 14H), 2.4–2.7 (m, 4H), 3.3–4.3 (m, 4H), 3.90 (s, 6H), 5.3–5.4 (m, 2H), 6.55 (d, J=16 Hz, 1H), 6.6–7.2 (m, 6H), 7.40 (d, J=16 Hz, 1H).

EXAMPLE 15-(2)

Preparation of 1-(3,4-dihydroxyphenyl)-6-(3,4-dimethoxyphenyl)-3-oxo-1-hexene

In 5 ml of absolute methanol was dissolved 100 mg of 1-(3,4-bistetrahydropyranyloxyphenyl)-6-(3,4-dimethoxyphenyl)-3-oxo-1-hexene obtained in Example 15-(1). A catalytic amount of p-toluenesulfonic acid was added to the solution at 0° C. and a stirring was effected at the same temperature for 1 hour. After the reaction, 1 drop of triethylamine was added to the reaction mixture and then the mixture was concentrated to give crude product. By purification of the crude product by means of column chromatography (silica gel/hexane:ethyl acetate=1:1), 55 mg of the above caption compound was obtained.

IR: γmax 3500, 1680, 1635, 975 cm$^{-1}$.

NMR: δ(D$_6$—DMSO), 1.2–1.6 (m, 2H), 2.4–2.7 (m, 4H), 3.85 (s, 6H), 6.50 (d, J=15 Hz, 1H), 6.6–7.2 (m, 6H), 7.40 (d, J=15 Hz, 1H), 8.70 (s, 1H), 9.51 (s, 1H).

EXAMPLE 16

In accordance with the above Examples 13-(1) and 13-(2) and the Referential Example 1, the following compounds were prepared:

Dimethyl 2-oxo-4-(3,4-dimethoxyphenyl)butylphosphonate

IR: γmax 1700, 1600, 1510 cm$^{-1}$.

NMR: δ(CDCl$_3$), 2.5–2.8 (m, 4H), 3.10 (d, J=24 Hz, 2H), 3.80 (d, J=12 Hz, 6H), 3.9 (s, 6H), 6.6–7.3 (m, 3H).

1,5-bis(3,4-dimethoxyphenyl)-3-oxo-1-pentene

IR: γmax 1690, 1640, 980 cm$^{-1}$.

NMR: δ(CDCl$_3$), 2.5–2.8 (m, 4H), 3.80 (2, 6H), 3.90 (s, 6H), 6.60 (d, J=16 Hz, 1H), 6.6–7.2 (m, 6H), 7.48 (d, J=16 Hz, 1H), 1,5-bis(3,4-dihydroxyphenyl)-3-oxo-1-pentene IR: γmax 3500, 1680, 1640, 980 cm$^{-1}$.

NMR: δ(D$_6$—DMSO), 2.5–2.8 (m, 4H), 6.53 (d, J=16 Hz, 1H), 6.6–7.2 (m, 6H), 7.40 (d, J=16 Hz, 1H), 8.60 (s, 1H), 8.75 (s, 1H), 9.10 (s, 1H), 9.36 (s, 1H).

EXAMPLE 17-(1)

Preparation of 1-(3,4-bistetrahydropyranyloxyphenyl)-1-hexene

To 1 ml of dry dimethyl sulfoxide was added 80 mg of sodium hydride (50% oil), and the mixture was stirred at 78° to 80° C. for 15 minutes. Then, 1.5 ml of dry dimethyl sulfoxide solution containing 686 mg of pentyl-triphenylphosphonium bromide was added dropwise to the mixture under cooling with water, and then the stirring was continued for further 20 minutes at room temperature. Then, the mixture was again cooled with water and 1.5 ml of dry dimethyl sulfoxide solution containing 251 mg of 3,4-bistetrahydroxypyranyloxybenzaldehyde (synthesized from 3,4-dihydroxybenzaldehyde and dihydropyran) was added thereto dropwise. After addition by dropping, the mixture was stirred at room temperature for 1 and half hour. The reaction mixture was then poured into ice-water and extracted with ether. The extract was washed with water and saturated aqueous sodium chloride solution, dried with magnesium sulfate and concentrated under reduced pressure to give crude product. By purification of the crude product by means of column chromatography [silica gel/ether:hexane (1:6)], 198 mg of pure product was obtained.

IR: γmax 1603, 1589, 961 cm$^{-1}$.

NMR: δ(CDCl$_3$), 0.92 (t, J=6 Hz, 3H), 1.1-2.1 (m, 16H), 2.1-2.6 (m, 2H), 3.35-4.30 (m, 4H), 5.44 (s, 2H), 5.45-6.5 (m, 2H), 6.75-7.20 (m, 3H).

EXAMPLE 17-(2)

Preparation of 1-(3,4-dihydroxyphenyl)-1-hexene

In 10 ml of absolute methanol was dissolved 198 mg of 1-(3',4'-bistetrahydropyranyloxy-phenyl)-1-hexene obtained in Example 17-(1), and a catalytic amount of p-toluenesulfonic acid was added to the solution at 0° C. The mixture was stirred for 2 hours at the same temperature. After reaction, one drop of triethylamine was added to the reaction mixture and the mixture was concentrated to give crude product. By purification of the crude product by means of column chromatography [silica gel/ether:hexane (1:2)], 61 mg of pure product was obtained.

IR: γmax 3300. 1600, 960 cm$^{-1}$.

NMR: δ(CDCl$_3$), 0.8-1.0 (m, 3H), 1.1-1.6 (m, 4H), 2.0-2.5 (m, 2H), 5.1 (s, 2H), 5.54 (d, t, J=11, 7 Hz, 1H), 6.27 (d, 1H, J=11 Hz), 6.7-7.0 (m, 3H).

EXAMPLE 18

Preparation of 1-(3,4-dihydroxyphenyl)-1-heptene

In accordance with Examples 17-(1) and 17-(2), 1-(3,4-dihydroxyphenyl)-1-heptene was prepared using hexyltriphenyl-phosphonium bromide.

IR: γmax 3320, 1600, 965 cm$^{-1}$.

NMR: δ(CDCl$_3$), 0.7-1.1 (m, 3H), 1.1-1.8 (m, 6H), 1.9-2.5 (m, 2H), 5.49 (d, t, J=11, 7 Hz, 1H), 5.7 (s, 2H), 6.23 (d, J=11 Hz, 1H), 6.7-6.93 (m, 3H).

EXAMPLE 19

Preparation of 1-(3,4-dihydroxyphenyl)-1-octene

In accordance with Examples 17-(1) and 17-(2), 1-(3,4-dihydroxyphenyl-1-octene was prepared using heptyltriphenyl-phosphonium bromide.

IR: γmax 3350, 1600, 960 cm$^{-1}$.

NMR: δ(CDCl$_3$), 0.7-1.05 (m, 3H), 1.05-1.7 (m, 8H), 1.9-2.5 (m, 2H), 5.52 (d, t, 1H, J=11, 7 Hz), 6.23 (d, 1H, J=7 Hz), 6.6-6.9 (m, 3H).

EXAMPLE 20

Preparation of 1-(3,4-dihydroxyphenyl)-4-phenyl-1-butene

In accordance with Examples 17-(1) and 17-(2), 1-(3,4-dihydroxyphenyl)-4-phenyl-1-butene was prepared.

However, 3-phenyl-n-propyl-1-triphenyl-phosphonium bromide synthesized from triphenylphosphine and 1-bromo-3-phenylpropane was used as the Wittig reagent.

IR: γmax 3350, 1600, 960 cm$^{-1}$.

NMR: δ(CDCl$_3$), 2.0-2.5 (m, 2H), 2.60 (t, J=6 Hz, 2H), 5.50 (d, t, J=11, 7Hz, 1H), 5.6 (s, 2H), 6.20 (d, J=11 Hz, 1H), 6.7-6.9 (m, 3H), 7.1 (s, 5H).

EXAMPLE 21

Preparation of 1-(3,4-dihydroxyphenyl)-4-(3,4-dimethoxyphenyl)-1-butene

In accordance with Examples 17-(1) and 17-(2), 1-(3,4-dihydroxyphenyl)-4-(3,4-dimethoxyphenyl)-1-butene was prepared.

However, 3-(3,4-dimethoxyphenyl)propyl-1-triphenyl-phosphonium bromide synthesized from triphenylphosphine and 1-bromo-3-(3,4-dimethoxyphenyl)propane [this compound was synthesized from 3-(3,4-dimethoxyphenyl)-1-propanol and phosphorus tribromide] was used as the Wittig reagent.

IR: γmax 3340, 1605, 965 cm$^{-1}$.

NMR: δ(CDCl$_3$), 2.0-2.5 (m, 2H), 2.60 (t, J=6 Hz, 2H), 3.9 (s, 6H), 5.55 (d, t, J=11, 7 Hz, 1H), 5.8 (s, 2H), 6.25 (d, J=11 Hz, 1H), 6.6-6.9 (m, 6H).

While the invention has been described in detail and with reference to specific embodiments thereof, it will be apparent to one skilled in the art that various changes and modifications can be made therein without departing from the spirit and scope thereof.

What is claimed is:

1. A lipoxygenase inhibitor composition comprising as active ingredient a lipoxygenase inhibiting effective amount of a substituted styrene derivative having formula (I)

(I)

wherein X represents a hydroxyl group or a lower alkoxy group, q is an integer of 2 or 3; and Y represents a member selected from the group consisting of —COOR$_1$ wherein R$_1$ represents an alkyl group having 4 to 10 carbon atoms, which may be substituted by halogen(s);

wherein R$_2$ and R$_3$ each represents a hydrogen atom, a lower alkoxy group or a hydroxyl group and Z represents a radical of the formula, —O—(CH$_2$)$_n$—CH=CH—, —NH—(CH$_2$)$_n$—CH=CH— or —NH—(CH$_2$)$_n$—, wherein n is an integer of 1 to 4; —CO—NH—C$_m$H$_{2m+1}$ wherein m is an integer of 6 to 14; —CO—(CH$_2$)$_l$—R$_4$ wherein R$_4$ represents a phenyl group which may be substituted by a hydroxyl group, a lower alkoxy group or a halogen atom, or a hydrogen atom and l is zero or an integer of 1 to 7, said l being an integer of 1 to 7 when said R$_4$ represents a hydrogen atom; and —C$_p$H$_{2p}$—R$_5$ wherein R$_5$ represents a hydrogen atom or a wherein R$_6$ and R$_7$ each represents a hydrogen atom, a hydroxyl group, a lower alkoxy group or a halogen atom and p is an integer of 1 to 8 when R$_5$ is a hydrogen atom, and zero or an integer of 1 to 5 when R$_5$ is and a pharmaceutically acceptable carrier.

2. A lipoxygenase inhibitor composition of claim 1, wherein the substituted styrene derivative is a compound represented by the general formula wherein $R_1$ denotes an alkyl group having 4 to 10 carbon atoms, which may be substituted by halogen(s), and X and q have the same meanings as defined in claim 1.

3. A lipoxygenase inhibitor composition of claim 1, wherein the substituted styrene derivative is a compound represented by the general formula wherein $R_2$ and $R_3$ each denotes a hydrogen atom, a lower alkoxy group or a hydroxyl group, Z denotes a radical of the formula

—O—(CH$_2$)$_n$—CH=CH—,

—NH—(CH$_2$)$_n$—CH=CH— or

—NH—(CH$_2$)$_n$— in which n is an integer of 1 to 4, and X and q have the same meanings as defined in claim 1.

4. A lipoxygenase inhibitor composition of claim 1, wherein the substituted styrene derivative is a compound represented by the general formula wherein m is an integer of 6 to 14 and X and q have the same meanings as defined in claim 1.

5. A lipoxygenase inhibitor composition of claim 1, wherein the substituted styrene derivative is a compound represented by the general formula wherein $R_4$ denotes a phenyl group which may be substituted by a hydroxyl group, a lower alkoxy group or a halogen atom, or a hydrogen atom, l is zero or an integer of 1 to 7, and X and q have the same meanings as defined in claim 1, said being an integer of 1 to 7 when said $R_4$ denotes a hydrogen atom.

6. A lipoxygenase inhibitor composition of claim 1 wherein the substituted styrene derivative is a compound represented by the general formula wherein $R_5$ denotes a hydrogen atom or a in which $R_6$ and $R_7$ each denotes a hydrogen atom, a hydroxyl group, a lower alkoxy group or a halogen atom, p is an integer of 1 to 8 when $R_5$ is a hydrogen atom, and zero or an integer of 1 to 5 when $R_5$ is and X and q have the same meanings as defined in claim 2.

* * * * *